United States Patent
Sanford

[11] Patent Number: 6,131,437
[45] Date of Patent: Oct. 17, 2000

[54] MECHANICAL CRUSH GAUGE AND METHOD OF USING SAME TO MEASURE FREE-FIELD ENERGY FLUX DENSITY

[75] Inventor: Matthew J. Sanford, Bel Alton, Md.

[73] Assignee: The United States of America as represented by the Secretary of the Navy, Washington, D.C.

[21] Appl. No.: 08/941,931

[22] Filed: Sep. 30, 1997

[51] Int. Cl.$^7$ ..................................................... G01N 3/30
[52] U.S. Cl. ..................... 73/12.09; 73/12.13; 73/35.14
[58] Field of Search ................................ 73/12.01, 12.04, 73/12.05, 12.06, 12.09, 12.13, 35.14, 35.15, 35.16

[56] References Cited

U.S. PATENT DOCUMENTS

| | | | |
|---|---|---|---|
| 2,415,436 | 2/1947 | Maris | 73/33.16 |
| 3,266,289 | 8/1966 | Stamy | 73/12.13 |
| 3,298,222 | 1/1967 | Costello et al. | 73/12.13 |
| 3,879,982 | 4/1975 | Schmidt | 73/12.09 |
| 4,198,869 | 4/1980 | Mayernik | 73/709 |
| 4,531,400 | 7/1985 | Nevel | 73/12.13 |
| 4,860,572 | 8/1989 | Brar et al. | 73/12.13 |

*Primary Examiner*—Max H. Noori
*Attorney, Agent, or Firm*—James B. Bechtel, Esq.

[57] ABSTRACT

A mechanical crush gauge has a housing defining a fixed diameter hole that holds a sample of deformable material and an indentor having a flat end and a spherically-shaped end opposite the flat end. The indentor has its flat end flush with the surface of the housing and its spherically-shaped end in tangential contact with the sample. The indentor is made from a material having a yield strength orders of magnitude greater than that of the sample. Energy absorbed by the flat end is converted into kinetic energy that forces the spherically-shaped end against the sample to form a spherical dent therein indicative of energy flux density. In use, the diameter of the spherical dent is measured and converted to an energy value indicative of energy absorbed by the sample per unit area of the flat end of the indentor. The energy value is then calibrated by a correction factor that accounts for an acoustic impedance mismatch between the mechanical crush gauge and the medium of energy transmission in order to arrive at the free-field energy in the medium.

19 Claims, 2 Drawing Sheets

MECHANICAL CRUSH GAUGE AND METHOD OF USING SAME TO MEASURE FREE-FIELD ENERGY FLUX DENSITY

ORIGIN OF THE INVENTION

The invention described herein was made in the performance of official duties by an employee of the Department of the Navy and may be manufactured, used, licensed by or for the Government for any governmental purpose without payment of any royalties thereon.

1. Field of the Invention

The invention relates generally to energy measurement, and more particularly to a mechanical crush gauge and a method of using the gauge to measure free-field energy flux density of an explosive event or events.

2. Background of the Invention

The clearing of mines is of great interest in the world today. In surf zones (i.e., in the water and/or in water-saturated sand), an apparatus used for mine clearing is a detonating cord net. Briefly a detonating cord net is a large net-like arrangement of strings of detonating cord. Detonating cord is a rope-like arrangement of a flexible explosive composition encased in a flexible outer sheath that contains and supports the explosive composition while serving as an environmental barrier. Such cord is commonly used in mining and other blasting operations to set off multiple charges at various locations simultaneously. When arranged in a net-like pattern and detonated, high shock levels can be supplied to a large area with relatively low weight of explosive material as compared to one or several isolated charges. The explosive output produced by a detonating cord net is not a single pulse or shock wave as is the case with a single explosive charge. Rather, a detonating cord net generates multiple shock waves which reach any specific point (i.e., the location of a single mine) at different times.

When the task involves damaging or destroying a mine, a certain minimum pressure level must be attained and maintained for sufficient time period in order for the mechanical work of damage to occur. Different types of mines require different levels of pressure and duration with higher pressure levels typically causing damage over a shorter time period. Multiple shocks of various duration (e.g., as delivered by detonating cord nets) further complicate the relationship between shock and damage. Thus, in order to predict the effectiveness of a detonating cord net, energy per unit area (or energy flux density as it is known) in the free field around the detonating cord net must be determined. Energy flux density is an indication of the energy traveling through a medium that is available to do work and is measured in units such as inch pounds per square inch. In terms of an explosive event, energy flux density indicates the energy available to cause damage.

A variety of mechanical and electronic gauges known in the prior art are designed to measure pressure or force per unit area. The mechanical gauges typically make use of copper balls that are deformed by a piston subjected to the explosive event. Ball deformation is measured as an indication of pressure. However, these balls must be made to extremely tight tolerances (e.g., on the order of 0.0002 inches or less). Further, mechanical pressure gauges are generally considered inaccurate when it comes to determining short duration peak pressures associated with explosive event shock waves because they require a relatively long time to react. With the advent of piezoelectric electronic pressure gauges, these mechanical gauges became obsolete with respect to measuring shock waves of an explosive event.

Piezoelectric electronic pressure gauges measure change in pressure over time. In terms of measuring the output of a detonating cord net, a piezoelectric gauge with a fast response time would record a jagged trace of multiple peaks spread over a period of time. To convert this to energy data, a first integration must be performed to obtain a pressure time curve. Then, a second integration must be performed on the pressure time curve with the results thereof being squared.

The problem is that each time the gauge data is integrated, accuracy decreases since baseline shifts inherent in the gauge are squared as are any gauge errors. The errors increase with the length of time of integration. Further, measurement data must be adjusted for the complexities of the measuring equipment such as the impedances and capacitances of the gauge, lead wires and cables, amplifiers and data recording equipment. Thus, electronic gauges involve not only expensive equipment, but also produce data that is expensive to interpret (i.e., requiring highly trained personnel) when the goal is to obtain energy data. Other disadvantages of using electronic gauges for measuring explosive event data include a limited number of gauges that can be used in a test due to their expense and/or a limited number of channels available for recording data. Also, wires leading to the gauges cannot be too long. Therefore, personnel operating the recording equipment must be located near the explosive event, or the recording equipment must be operated remotely which can be even more difficult and expensive.

SUMMARY OF THE INVENTION

Accordingly, it is an object of the present invention to provide a gauge that can be used to determine energy flux density of an explosive event.

Another object of the present invention is to provide a gauge that can be used to determine energy flux density that is of simple construction, is simple to use and produces data that is simple to interpret.

Yet another object of the present invention is to provide a gauge that can be used to determine a broad range of energy flux densities.

Other objects and advantages of the present invention will become more obvious hereinafter in the specification and drawings.

In accordance with the present invention, a mechanical crush gauge has a housing defining a fixed diameter hole with a first end at a surface of the housing and a second end within the housing. A sample of deformable material is positioned in the fixed diameter hole and is sized to loosely fit therein at the second end. An indentor having a flat end and a spherically-shaped end opposite the flat end is coaxially positioned and sealed within the fixed diameter hole for sliding movement therein. The indentor has its flat end flush with the surface of the housing. The indentor is made from a material having a yield strength orders of magnitude greater than that of the sample. The spherically-shaped end is in tangential contact with the sample. Energy absorbed by the flat end is converted into kinetic energy that forces the spherically-shaped end against the sample to form a spherical dent therein indicative of energy flux density.

In use, the diameter of the spherical dent is measured and converted to an energy value indicative of energy absorbed by the sample per unit area of the flat end of the indentor. The energy value is then calibrated or multiplied by a correction factor that accounts for an acoustic impedance mismatch between the mechanical crush gauge and the medium of energy transmission in order to arrive at the free-field energy in the medium.

DETAILED DESCRIPTION OF THE INVENTION

Figure 1:
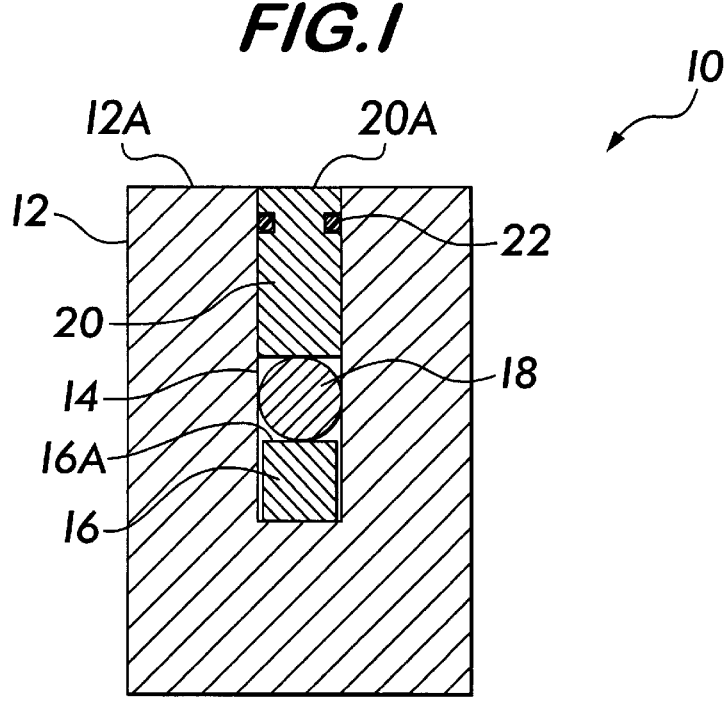
FIG. 1 is a cross-sectional view of an embodiment of the mechanical crush gauge of the present invention prior to its being exposed to an explosive event.

Referring now to the drawings, and more particularly to FIG. 1, an embodiment of the mechanical crush gauge of the present invention is shown and referenced generally by the numeral 10. By way of illustrative example, gauge 10 will be described for its use in determining energy flux density of an explosive event. However, it is to be understood that the present invention could also be used in the determination of energy flux density associated with other types of events.

Gauge 10 includes a rigid housing 12 having a cylindrical hole 14 formed therein. Positioned within hole 14 are a dent sample 16 at the bottom of hole 14, a ball 18 resting on or in tangential contact with sample 16, and a piston 20 resting on or in tangential contact with ball 18. In the present invention, the fit of each of sample 16, ball 18, and piston 20 within hole 14 is important.

Sample 16 is sized to loosely fit within hole 14 where "loosely fit" is defined herein to mean that sample 16 is allowed to slide in hole 14 without sticking or dragging, yet not be allowed to experience appreciable side-to-side motion. Any sticking or dragging of sample 16 in hole 14 could result in the absorption of energy of motion (as will be explained further below) of ball 18 and piston 20, thereby affecting results. Too loose a fit permits sample deformation that complicates the measurement process.

Ball 18 is sized to slide within hole 14. That is, ball 18 should be sized such that it is large enough to keep from bouncing from side to side in hole 14, but small enough so that it is not restricted from axial movement within hole 14. For measuring explosive events, piston 20 should have a length-to-diameter ratio of at least approximately two. The longer length of piston 20 relative to its diameter allows for good transfer of absorbed energy into kinetic energy as will be explained below. Piston 20 must also form a good seal with the sides of hole 14, but still be able to move axially within hole 14. Accordingly, an O-ring type seal 22 can be provided annularly about piston 20 as is known in the art. Finally, hole 14 is of a length that will cause end face 20A of piston 20 to align with the surface 12A of housing 12.

Material selection for each of sample 16, ball 18 and piston 20 is also important in the present invention. In general, ball 18 and piston 20 should be made from a material having a yield strength that is orders of magnitude larger (e.g., at least twenty times as great) than that of sample 16. More specifically, ball 18 and piston 20 can be made from a high-strength steel having a yield strength on the order of 200,000 pounds per square inch. Sample 16 can be made from a softer, deformable material such as lead or copper which have yield strengths on the order of 1500 and 10,000 pounds per square inch, respectively. Note that housing 12 must be rigid and could also be made of steel.

Figure 2:
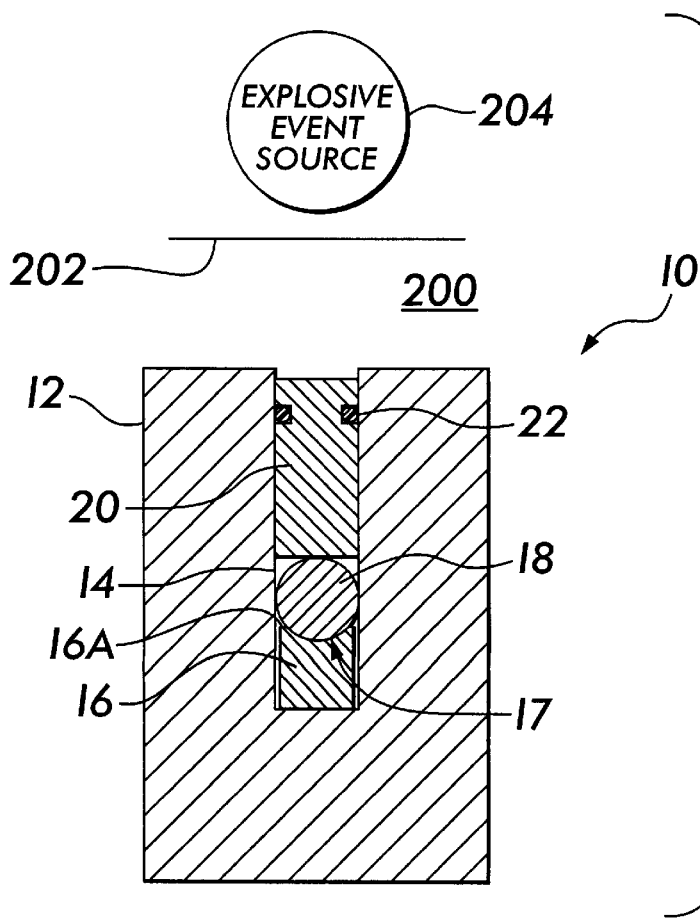
FIG. 2 is a cross-sectional view of the mechanical crush gauge after it has been exposed to an explosive event.

Once constructed as shown in FIG. 1, gauge 10 can be placed for measurement with face 20A of piston 20 arranged to face the direction of the source of an explosive event. As shown in FIG. 2, gauge 10 is positioned in the free-field 200 in which a shock wave 202 propagates from an explosive event source 204. Shock wave energy absorbed by piston 20 at face 20A is converted to kinetic energy causing piston 20 to move axially in hole 14 against ball 18. Since ball 18 and piston 20 are both made of high yield strength materials, the kinetic energy causes piston 20 and ball 18 to move axially together such that ball 18 is pressed into the much softer sample 16 which is constrained from axial movement within hole 14. As will be explained further below, the resulting dent 17 formed in surface 16A of sample 16 is indicative of energy flux density in free-field 200.

The spherical shape of ball 16 means that the cross-sectional area of dent 17 increases with the application of additional force/energy, but at a diminishing rate. This allows the gauge of the present invention to be sensitive to small variations in energy at the low end of the measurable energy range, yet still be able to measure variations at the high end of the measurement range. The use of different materials for sample 16 allows for a further extension of the measurement range. For example, sample 16 could be lead for lower energy measurements while copper could be used for higher energy measurements.

Figure 3:
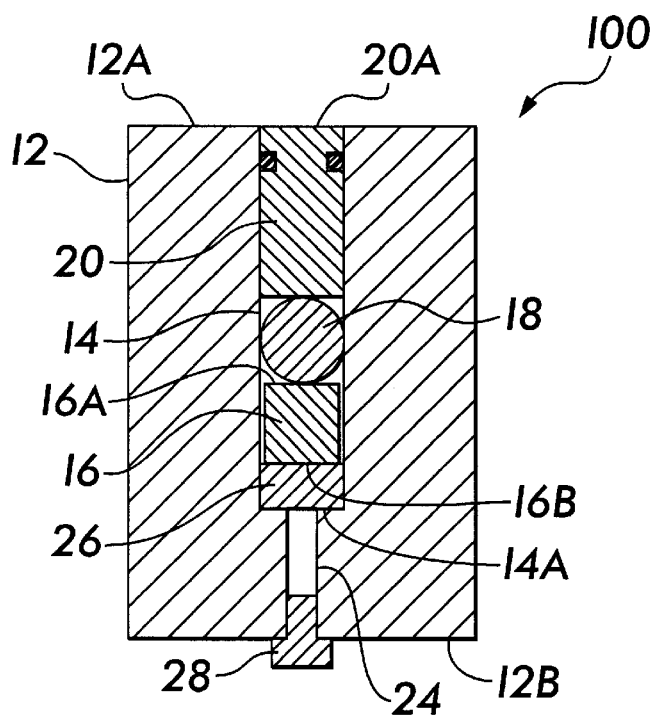
FIG. 3 is a cross-sectional view of another embodiment of the mechanical crush gauge that facilitates removal of the dent sample.

Another embodiment of the present invention is shown in FIG. 3 and is referenced generally by numeral 100. Like reference numerals are used for those elements that are common with the embodiment shown in FIGS. 1 and 2. In gauge 100, housing 12 has a second hole 24 formed therein that is coupled to and is coaxial with hole 14. Second hole 24 is accessible at surface 12B of housing 12 which is opposite surface 12A. Second hole 24 is of smaller diameter than hole 14 such that the intersection of holes 14 and 24 forms an annular shoulder 14A defining the bottom of hole 14. A shim 26 of high yield strength material (e.g., high strength steel) is placed between shoulder 14A and sample 16. Prior to use, a removable plug or seal 28 seals hole 24. The other elements and their relationship to hole 14 for gauge 100 are as described above for gauge 10.

The additional features of gauge 100 allow sample 16 to be used in two measurements and further facilities the removal of sample 16 after use. More specifically, after being placed and used (similar to that described above for gauge 10), plug 28 is removed. A pin (not shown) or other thin implement is inserted into second hole 24 and pressed against shim 26 in order to push out (dented) sample 16, ball 18 and piston 20. The presence of shim 26 protects face 16B so that sample 16 can be flipped over and used in another measurement.

Figure 4:
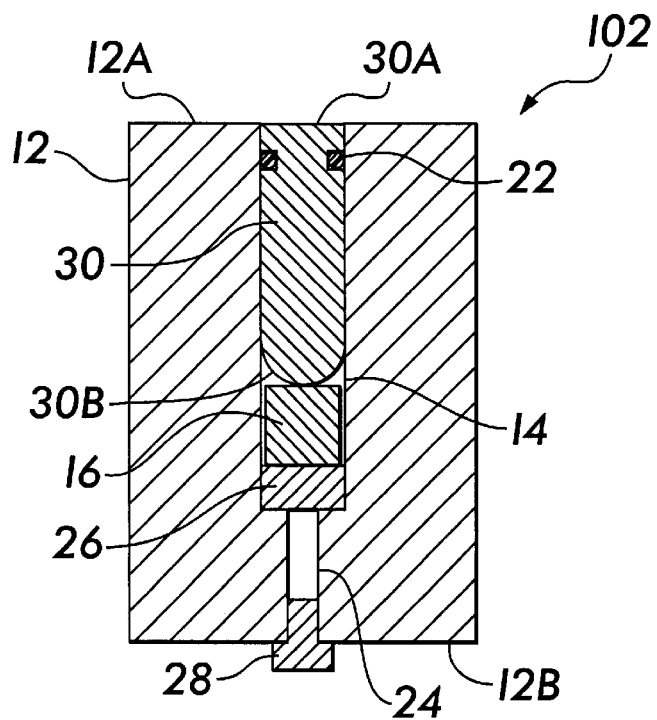
FIG. 4 is a cross-sectional view of still another embodiment of the mechanical crush gauge.

Although gauges 10 and 100 both make use of a conventional piston shape and conventional ball, the present invention is not so limited. As shown in FIG. 4, gauge 102 replaces ball 18 and piston 20 with a single penetrator or indentor 30. Indentor 30 is cylindrical and has a flat end 30A that will be flush with surface 12A of housing 12. Indentor 30 also has a spherically-shaped end 30B. Similar to ball 18 and piston 20, indentor 30 would be made of, for example, a high strength steel. Regardless of the construction of the mechanical crush gauge of the present invention, the gauge is positioned in a medium and the diameter of the resulting dent 17 in sample 16 is measured as described above for gauge 10.

To convert the diameter of a dent 17 into an energy value, the mechanical crush gauge of the present invention must be calibrated. In general, such calibration requires that known amounts of energy be applied to piston 20 (or indentor 30) with the diameter of the resulting dent 17 being measured/recorded for each applied known amount of energy. This could be accomplished using one of the many standard compression testers capable of applying a load to a sample and measuring the resulting deflection. As a result, a curve can be produced showing the relationship between energy absorbed and dent diameter. This calibration data can then be used to relate a dent diameter to an energy absorbed by piston 20 (or indentor 30) due to an explosive event. However, the energy absorbed by the piston is not the free-field energy. This is because a source of error that must be accounted for is the acoustic impedance mismatch between the gauge and the medium of shock wave transmission (e.g., water or saturated sand in the case of mines).

Sound, or shock waves in the case of an explosive event, traveling through a medium tends to partially transmit and partially reflect at the interface of a new medium, e.g., the gauge of the present invention. More specifically, piston 20 (or indentor 30) will only absorb part of the energy per unit area of the shock wave and reflect the rest. The amount of energy absorbed and reflected is based on the density of each medium, the speed of sound in each medium, and the duration and intensity of the pulse to be measured. Thus, it is necessary to determine an acoustic impedance mismatch correction factor to convert the energy absorbed by the piston into a free-field measurement.

One way to determine the correction factor is to compare energy data from a mechanical gauge of the present invention to energy data derived from a piezoelectric gauge placed adjacent the mechanical gauge. Alternatively, the correction factor can be determined analytically. For example, the correction factor F for a piston 20 made of steel and a free-field 200 that is water could be determined as follows.

The acoustic impedance $Z_s$ of piston 20 is given by:

$$Z_s = \rho_s \times U_s \quad (1)$$

where $\rho_s$ is the density of steel or $7.8 \times 10^3$ kg/m$^3$ and $U_s$ is the speed of sound in steel or $5 \times 10^3$ m/s so that $Z_s = 39 \times 10^6$ kg/m$^2$s. The approximate pressure-speed of sound curve for steel in the 10–50 Kilo-psi range is linear and is of the form:

$$P_s = (4 \times 10^7) U_s \quad (2)$$

where the units of $P_s$ is pascal and the units of the constant of $4 \times 10^7$ are kg/m$^2$s.

The acoustic impedance $Z_w$ of water is given by:

$$Z_w = \rho_w \times U_w \quad (3)$$

where $\rho_w$ is the density of water or 1000 kg/m$^3$ and $U_w$ is the speed of sound in water which, at the test site, was 1497 m/s. The resulting $Z_w = 1.497 \times 10^6$ kg/m$^2$s. The approximate pressure-speed of sound curve for water in the 10–50 Kilo-psi range is of the form:

$$P_w = \left(1.483 + 10.99 \ln\left(1 + \frac{U_s}{5190}\right)(U_s)\right)(1 \times 10^6) \quad (4)$$

In general, energy E can be approximated by:

$$E \approx \frac{P^2}{Z} \quad (5)$$

with the ratio of energy in the free-field or $E_{TOTAL}$ to energy absorbed by piston 20 or $E_{ABSORBED}$ being the correction factor F as given by $$F = \frac{E_{TOTAL}}{E_{ABORBED}} \approx \frac{\left(\frac{P_w^2}{Z_w}\right)}{\left(\frac{P_s^2}{Z_s}\right)} \quad (6)$$

or $$F = \frac{E_{TOTAL}}{E_{ABORBED}} \approx \left(\frac{P_w^2}{P_s^2}\right)\left(\frac{Z_s}{Z_w}\right) \quad (7)$$

Note that equation (7) is for a first reflection only. Using equation (7) and values for $P_s$ and $P_w$ from equations (2) and (4), the correction factor F can be determined analytically for one or more values of pressures. Note that this pressure ratio varies very slowly in the pressure and frequency range generated by a typical detonating cord net.

The advantages of the present invention are numerous. It is a simple and inexpensive gauge to build and use for determining free-field energy flux density. The gauge is well-suited to be used in large numbers to effectively map the energy flux density associated with a multiple explosive event device such as detonating cord nets. Once calibrated for a medium, the gauge and method of using same will allow even unskilled personnel to determine energy flux density. Further, in terms of explosive events, the gauge of the present invention is extremely safe to use since no personnel need be in a position to record any data electronically.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A mechanical crush gauge for measuring energy flux density associated with a shock wave propagating in a wet free-field environment, comprising:

a housing defining a fixed diameter hole having a first end at a surface of said housing and a second end within said housing;

a sample of deformable material positioned in said fixed diameter hole and sized to loosely fit therein at said second end;

a piston and ring assembly positioned in said fixed diameter hole with one face of said piston being flush with said surface of said housing, said ring sealing said piston in said fixed diameter hole and positioning said piston coaxially therein, said piston made from a material having a yield strength orders of magnitude greater than that of said sample; and a ball positioned in said hole between said sample and said piston, said ball being in tangential contact with said sample and said piston, said ball sized to slide in said fixed diameter hole, said ball being made from a material having a yield strength approximately equivalent to said yield strength of said piston, wherein energy absorbed by said piston at said one face thereof is converted into kinetic energy that forces said piston against said ball and said ball against said sample to form a spherical dent in said sample, and wherein said spherical dent is indicative of energy flux density.

2. A mechanical crush gauge as in claim 1 wherein said housing has a second hole formed therein that couples said second end of said fixed diameter hole to another surface of said housing opposite said surface of said housing at which said first end of said fixed diameter hole resides, said second hole being of smaller diameter than said fixed diameter hole, and further comprising a removable seal for sealing said second hole.

3. A mechanical crush gauge as in claim 2 wherein said second hole is coaxially aligned with said fixed diameter hole.

4. A mechanical crush gauge as in claim 2 further comprising a shim disposed in said fixed diameter hole between said sample and said second end of said fixed diameter hole.

5. A mechanical crush gauge as in claim 1 wherein said piston and said ball are made of high strength steel.

6. A mechanical crush gauge as in claim 1 wherein said sample is made from a material selected from the group consisting of lead and copper.

7. A mechanical crush gauge as in claim 1 wherein said piston has a length-to-diameter ratio of at least approximately two.

8. A mechanical crush gauge for measuring energy flux density associated with a shock wave propagating in a wet free-field environment, comprising:

a housing defining a fixed diameter hole having a first end at a surface of said housing and a second end within said housing;

a sample of deformable material positioned in said fixed diameter hole and sized to loosely fit therein at said second end; and an indentor having a flat end and a spherically-shaped end opposite said flat end, said indentor coaxially positioned and sealed within said fixed diameter hole for sliding movement therein, said indentor positioned in said fixed diameter hole with said flat end flush with said surface of said housing, said indentor made from a material having a yield strength orders of magnitude greater than that of said sample, said spherically-shaped end being in tangential contact with said sample, wherein energy absorbed by said flat end is converted into kinetic energy that forces said spherically-shaped end against said sample to form a spherical dent therein indicative of energy flux density.

9. A mechanical crush gauge as in claim 8 wherein said housing has a second hole formed therein coaxially aligned with said fixed diameter hole for coupling said second end of said fixed diameter hole to another surface of said housing opposite said surface of said housing at which said first end of said fixed diameter hole resides, said second hole being of smaller diameter than said fixed diameter hole, and further comprising a removable seal for sealing said second hole.

10. A mechanical crush gauge as in claim 9 further comprising a shim disposed in said fixed diameter hole between said sample and said second end of said fixed diameter hole.

11. A mechanical crush gauge as in claim 8 wherein said indentor is made of high strength steel.

12. A mechanical crush gauge as in claim 8 wherein said sample is made from a material selected from the group consisting of lead and copper.

13. A mechanical crush gauge as in claim 8 wherein said indentor has a length-to-diameter ratio of at least approximately two.

14. A mechanical crush gauge for measuring energy flux density associated with a shock wave propagating in a wet free-field environment, comprising:

a housing defining a fixed diameter hole having a first end at a surface of said housing and a second end within said housing, said housing further having a second hole formed therein that is coaxially aligned with and is coupled to said second end of said fixed diameter hole, said second hole extending to another surface of said housing opposite said surface of said housing at which said first end of said fixed diameter hole resides, said second hole being of smaller diameter than said fixed diameter hole;

a removable plug for sealing said second hole;

a sample of deformable material positioned in said fixed diameter hole and sized to loosely fit therein at said second end thereof;

a piston and ring assembly positioned in said fixed diameter hole with one face of said piston being flush with said surface of said housing, said ring sealing said piston in said fixed diameter hole and positioning said piston coaxially therein, said piston having a length-to-diameter ratio of at least approximately two, said piston further being made from a material having a yield strength orders of magnitude greater than that of said sample; and a ball positioned in said hole between said sample and said piston, said ball being in tangential contact with said sample and said piston, said ball sized to slide in said fixed diameter hole, said ball being made from a material having a yield strength approximately equivalent to said yield strength of said piston, wherein energy absorbed by said piston at said one face thereof is converted into kinetic energy that forces said piston against said ball and said ball against said sample to form a spherical dent in said sample, and wherein said spherical dent is indicative of energy flux density.

15. A mechanical crush gauge as in claim 14 further comprising a shim disposed in said fixed diameter hole between said sample and said second end of said fixed diameter hole.

16. A mechanical crush gauge as in claim 14 wherein said piston and said ball are made of high strength steel.

17. A mechanical crush gauge as in claim 14 wherein said sample is made from a material selected from the group consisting of lead and copper.

18. A method of determining free-field energy of an explosive event's shock wave propagating in a wet free-field environment, comprising the steps of:

providing a mechanical crush gauge that includes a housing defining a fixed diameter hole terminating therein, a sample of deformable material loosely fitted in said fixed diameter hole, and an indentor coaxially aligned in and in sealing engagement with said fixed diameter hole, wherein said indentor has a flat end flush with a surface of said housing and a spherically-shaped end in tangential contact with said sample;

positioning said mechanical crush gauge in a medium that is to experience the explosive event with said flat end of said indentor facing in a direction from which the explosive event will originate, wherein energy from the explosive event absorbed by said flat end is converted into kinetic energy that forces said spherically-shaped end against said sample to form a spherical dent therein;

measuring a diameter of said spherical dent;

converting said diameter to an energy value indicative of energy absorbed by said sample per unit area of said flat end; and calibrating said energy value using a correction factor that accounts for an acoustic impedance mismatch between said mechanical crush gauge and said medium, wherein said energy value so-calibrated is the free-field energy of the explosive event.

19. A method according to claim 18 wherein said step of converting comprises the steps of:

providing a test sample of deformable material loosely fitted in said fixed diameter hole;

applying a plurality of known amounts of energy directly to said indentor to form a corresponding plurality of dents in said test sample;

recording a diameter of each of said plurality of dents as a function of the corresponding one of said plurality of known amounts of energy; and selecting one of said plurality of known amounts of energy as said energy value based on a closest-fit comparison between said diameter of said spherical dent and each said diameter of said plurality of dents, wherein one said diameter of said plurality of dents that most closely approximates said diameter of said spherical dent is indicative of said one of said plurality of known amounts of energy.

* * * * *